(12) United States Patent
Arora et al.

(10) Patent No.: US 7,495,015 B2
(45) Date of Patent: Feb. 24, 2009

(54) INDAZOLE DERIVATIVES AND METHODS FOR USING THE SAME

(75) Inventors: Nidhi Arora, Cupertino, CA (US); Tobias Gabriel, San Francisco, CA (US); David Michael Goldstein, San Jose, CA (US); Teresa Alejandra Trejo-Martin, Union City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 595 days.

(21) Appl. No.: 11/065,979

(22) Filed: Feb. 25, 2005

(65) Prior Publication Data

US 2005/0215595 A1  Sep. 29, 2005

Related U.S. Application Data

(60) Provisional application No. 60/548,585, filed on Feb. 27, 2004.

(51) Int. Cl.
*A61K 31/4439* (2006.01)

(52) U.S. Cl. ............ 514/338; 514/406; 548/361.5

(58) Field of Classification Search ............ 514/338, 514/406; 548/361.5; 546/275.7
See application file for complete search history.

(56) References Cited

U.S. PATENT DOCUMENTS

| | | | |
|---|---|---|---|
| 3,948,913 A | | 4/1976 | Howarth et al. |
| 4,020,072 A | | 4/1977 | Hoehn |
| 4,044,130 A | | 8/1977 | Howarth et al. |
| 7,135,575 B2 * | | 11/2006 | Munson et al. ......... 548/361.1 |
| 2003/0207900 A1 | | 11/2003 | Chen et al. |
| 2004/0176325 A1 | | 9/2004 | Munson et al. |
| 2004/0180896 A1 | | 9/2004 | Munson et al. |

FOREIGN PATENT DOCUMENTS

| | | |
|---|---|---|
| DE | 2052719 | 9/1971 |
| EP | 0 104 522 B1 | 5/1991 |
| EP | 1 148 054 A1 | 10/2001 |
| WO | WO 98/09961 A1 | 3/1998 |
| WO | WO 99/23077 A1 | 5/1999 |
| WO | WO 00/27627 A1 | 5/2000 |
| WO | WO 01/02369 A2 | 1/2001 |
| WO | WO 01/98301 A1 | 12/2001 |
| WO | WO 02/22586 A1 | 3/2002 |
| WO | WO 02/051837 A2 | 7/2002 |
| WO | WO 02/059088 A1 | 8/2002 |
| WO | WO 03/000187 A2 | 1/2003 |
| WO | WO 03/009852 A1 | 2/2003 |
| WO | WO 03/029209 A2 | 4/2003 |
| WO | WO 03/051847 A1 | 6/2003 |
| WO | WO 03/062392 A2 | 7/2003 |
| WO | WO 03/068754 A1 | 8/2003 |
| WO | WO 03/099820 A1 | 12/2003 |

* cited by examiner

*Primary Examiner*—Kamal A Saeed
(74) *Attorney, Agent, or Firm*—Robert C. Hall

(57) ABSTRACT

Compounds of the formula I:

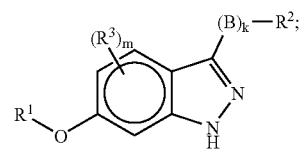

or pharmaceutically acceptable salts, solvates or prodrugs thereof,
wherein m, k, B, $R^1$, $R^2$ and $R^3$ are those defined herein, and compositions comprising the same. Also provided are methods for preparing compounds of formula I and using the same in treating p38 mediated disorders in a patient.

8 Claims, No Drawings

INDAZOLE DERIVATIVES AND METHODS FOR USING THE SAME

CROSS REFERENCE TO RELATED APPLICATIONS

This application claims benefit under 35 U.S.C. 119(e) of U.S. Provisional Application No. 60/548,585 filed Feb. 27, 2004, which is hereby incorporated by reference in its entirety.

FIELD OF THE INVENTION

The present invention relates to indazole derivatives, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J Exp. Opin. Ther. Patents,* 2000, 10(1).

The inhibition of these cytokines by inhibition of the p38 kinase is of benefit in controlling, reducing and alleviating many of these disease states.

SUMMARY

The invention provides compounds of the formula I:

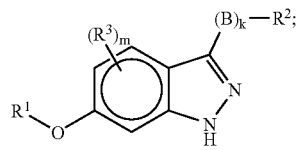

or pharmaceutically acceptable salts, solvates or prodrugs thereof, wherein:
  $R^1$ is aryl, heteroaryl, aralkyl or cycloalkyl;
  $R^2$ is aryl, heteroaryl, cycloalkyl or heterocyclyl;
  m is from 0 to 4;
  $R^3$ is hydrogen, alkyl, haloalkyl, cyano, nitro, amino, hydroxyl, alkoxy, heteroalkyl, heterocyclyl, hydroxycycloalkyl or
  —C(=O)—$R^a$,
    wherein
      $R^a$ is hydrogen, alkyl, heteroalkyl, aryl, aralkyl, heteroaryl or heterocyclyl;
    k is 0 or 1;
    B is O, S(O)$_j$, CH(OR$^b$), NR$^C$, or or C(=O),
    wherein
      j is 0, 1 or 2;
      $R^b$ is hydrogen or alkyl,
      $R^c$ is hydrogen, alkyl, —C(=O)—$R^d$, or —SO$_2$R$^e$,
      wherein
        $R^d$ is alkyl, aryl or aralkyl; and
        $R^e$ is alkyl.

Another aspect of the present invention provides a pharmaceutical formulation comprising one or more compounds of formula I and a pharmaceutically acceptable carrier, diluent, and/or excipient therefor.

Compounds of the invention are inhibitors of protein kinases, and exhibit effective activity against p38 in vivo. They are selective against p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Amino" means a radical -NR'R, where R' and R each independently is hydrogen or alkyl.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula $Ar^a$—$R^z$—, where $Ar^a$ is optionally substituted aryl and $R^z$ is alkylene as defined herein.

"Substituted aralkyl" or "optionally substituted aralkyl" refers to aralkyl in which the aryl moiety is substituted or optionally substituted, respectively.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula $R^c$—$R^d$—, where $R^c$ is cycloalkyl and $R^d$ is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl moiety as defined herein wherein one or more, preferably one, two or three, hydrogen atoms have been replaced with a substituent independently selected from the group consisting of —$OR^a$, —$NR^bR^c$ (where n is 0 or 1 if $R^b$ and $R^c$ are both independently alkyl, cycloalkyl or cycloalkylalkyl, and 0 if not) and —$S(O)_nR^d$ (where n is an integer from 0 to 2), with the understanding that the point of attachment of the heteroalkyl moiety is through a carbon atom, wherein $R^a$ is hydrogen, acyl, alkoxycarbonyl, alkyl, cycloalkyl, or cycloalkylalkyl; $R^b$ and $R^c$ are independently of each other hydrogen, acyl, alkoxycarbonyl, alkyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, $R^d$ is hydrogen, alkyl, cycloalkyl, cycloalkylalkyl, or aryl, and when n is 1 or 2, $R^d$ is alkyl, cycloalkyl, cycloalkylalkyl, or optionally substituted phenyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]pyridinyl, imidazo[2,1-b]thiazolyl, and the derivatives thereof.

"Heteroarylalkyl" refers to a moiety of the formula $Ar^z$—$R^y$—, where $Ar^z$ is heteroaryl and $R^y$ is alkylene as defined herein.

"Heterocyclyl" means a saturated or unsaturated non-aromatic cyclic moiety of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —$(X)_n$—C(O)$R^e$ (where X is O or $NR^f$, n is 0 or 1, $R^e$ is hydrogen, alkyl, haloalkyl, hydroxy (when n is 0), alkoxy, amino, mono- and dialkylamino, or optionally substituted phenyl, and $R^f$ is H or alkyl), -alkylene-C(O)$R^g$ (where $R^g$ is alkyl, —$OR^h$ or $NR^iR^j$ and $R^h$ is hydrogen, alkyl or haloalkyl, and $R^i$ and $R^j$ are independently hydrogen or alkyl), and —$S(O)_nR^k$ (where n is an integer from 0 to 2) such that when n is 0, $R^k$ is hydrogen, alkyl, cycloalkyl, or cycloalkylalkyl, and when n is 1 or 2, $R^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —$S(O)_nR^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, $2^{nd}$ ed. 1991) and Harrison and Harrison et al., *Compendium of synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

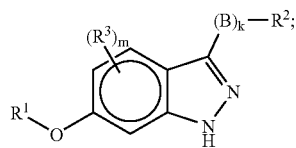

I or pharmaceutically acceptable salts, solvates or prodrugs thereof, wherein:
$R^1$ is aryl, heteroaryl, aralkyl or cycloalkyl;
$R^2$ is aryl, heteroaryl, cycloalkyl or heterocyclyl;
m is from 0 to 4;
$R^3$ is hydrogen, alkyl, haloalkyl, cyano, nitro, amino, hydroxyl, alkoxy, heteroalkyl, heterocyclyl, hydroxycloalkyl or
—C(=O)—$R^a$,
wherein
$R^a$ is hydrogen, alkyl, heteroalkyl, aryl, aralkyl, heteroaryl or heterocyclyl;
k is 0 or 1;
B is O, S(O)$_j$, CH(OR$^b$), NR$^c$, or or C(=O),
wherein
j is 0, 1 or 2;
$R^b$ is hydrogen or alkyl,
$R^c$ is hydrogen, alkyl, —C(=O)—$R^d$, or —SO$_2$R$^e$,
wherein
$R^d$ is alkyl, aryl or aralkyl; and
$R^e$ is alkyl.

In embodiments of the invention where any of $R^1$, $R^2$, $R^3$, $R^a$, $R^b$, $R^c$ or $R^d$ is alkyl or contains an alkyl moiety, such alkyl is preferably lower alkyl, i.e. $C_1$-$C_6$alkyl, and more preferably $C_1$-$C_4$alkyl.

In many embodiments, k is 0.

In certain embodiments k is 1 and B is NR$^b$.

In certain embodiments, $R^2$ is optionally substituted phenyl, optionally substituted thienyl, or optionally substituted pyridyl. Preferably, $R^2$ is 2-chlorophenyl, 4-hydroxyphenyl, 4-methoxyphenyl, 4-benzyloxyphenyl, 3-benzyloxyphenyl, 4-dimethylaminophenyl, 4-aminophenyl,4-fluorophenyl, 3-fluorophenyl, 2-fluorophenyl, 3-trifluoromethylphenyl, pyrid-3-yl, 4-(pyrid-2-yl)phenyl, 3-isopropoxyphenyl, 3,5-dimethylphenyl, 1,3-benzodioxol-5-yl, 3-morpholinophenyl, 4-morpholinophenyl, 3-(4-methyl-piperazin-1-yl)-phenyl, 4-(4-methyl-piperazin-1-yl)-phenyl, N-methyl-N-(2-methoxyethyl)-phenyl, or 2,4-difluorophenyl, 4-isopropyloxyphenyl, 3-(2-pyridin-2-yl-ethoxy)-phenyl, thien-2-yl, benzothiophen-3-yl, benzothiophen-2-yl, furan-2-yl, benzofuran-4-yl, indole-3-yl, 3-chloro-4-propoxyphenyl, biphenyl, pyridin-3-ylphenyl, and 3,4,5-trimethoxyphenyl. In embodiments wherein R2 is heterocyclyl, $R^2$ may be piperazinyl, morpholinyl, thiomorpholinyl, tetrahydrofuranyl, tetrahydrothiofuranyl, 1,1-dioxythiomorpholinyl, or 1,1-dioxytetrahydrothiofuranyl.

In certain embodiments, $R^1$ is optionally substituted phenyl, such as 2-halophenyl or 2,4-dihalophenyl. More specifically, $R^1$ may be 2,4-difluorophenyl, 4-fluorophenyl, 3-fluorophenyl, 2-fluorophenyl, phenyl, 2-chlorophenyl, 3,4-difluorophenyl, 4-trifluoromethylphenyl, 3-trifluoromethylphenyl, 2-trifluoromethylphenyl, 4-methylphenyl, 4-methoxyphenyl, 3,4-dichlorophenyl, 1,3-benzodioxol-5-yl, methyl, isopropyl, cyclohexyl, and 2,4-difluorobenzyl. More preferred are 2-halophenyl and 2,4-dihalophenyl, and most preferred is 2-fluorophenyl.

The compounds of the invention can exist in unsolvated forms as well as solvated forms, including hydrated forms. In general, the solvated forms, including hydrated forms, are equivalent to unsolvated forms and are intended to be encompassed within the scope of the present invention. In addition to the compounds described above, the compounds of the present invention include all tautomeric forms. Furthermore, the present invention also includes all pharmaceutically acceptable salts of those compounds along with prodrug forms of the compounds and all stereoisomers whether in a pure chiral form or a racemic mixture or other form of mixture.

The compounds of formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

In certain embodiments wherein k is 0, the compounds of the invention may be represented by the formula II:

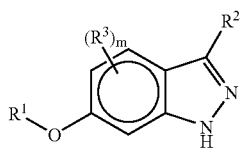

II wherein A, $R^1$, $R^2$, m and $R^3$ are as defined above.

In certain embodiments of formula II, $R^1$ and $R^2$ may both be optionally substituted phenyl, such that the compounds of the invention are of the formula III:

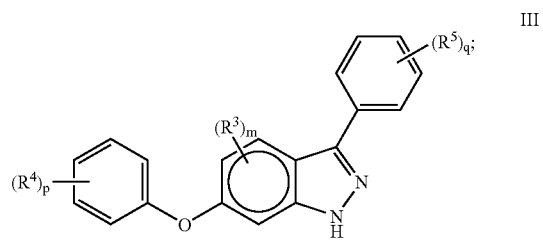

III wherein:
p and q each independently is from 0 to 4;
each $R^4$ is independently halo, alkyl, alkoxy, haloalkyl, or cyano;
each $R^5$ is independently halo, alkyl, haloalkyl, cyano, heteroalkyl, heterocyclyl, hydroxycycloalkyl or —C(=O)—$R^e$,
wherein
$R^e$ is alkyl, heteroalkyl, aryl, aralkyl, heteroaryl or heterocyclyl; and
m and $R^3$ are as defined herein.

In certain embodiments of formula III wherein $R^3$ is hydrogen, the compounds of the invention may be represented by formul IV:

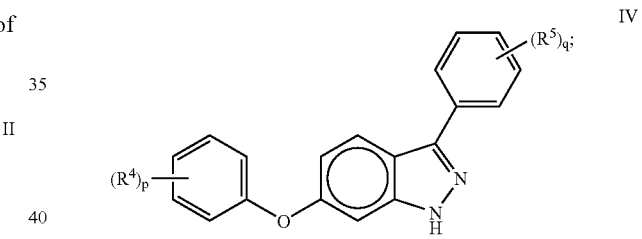

IV wherein p, q, $R^4$ and $R^5$ are as defined herein.

Representative compounds in accordance with the invention are shown below in Table 1.

TABLE 1

| # | Structure | Name (Autonom ™) | MP ° C. or M + H |
|---|-----------|------------------|------------------|
| 1 | ![structure] | 6-(2-Fluoro-phenoxy)-3-phenyl-1H-indazole | 305 |

TABLE 1-continued

| # | Structure | Name (Autonom ™) | MP ° C. or M + H |
|---|---|---|---|
| 2 | 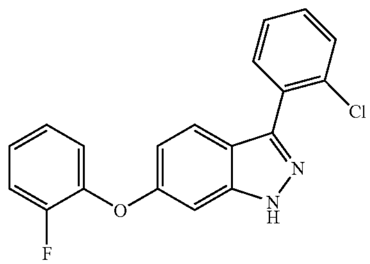 | 3-(2-Chloro-phenyl)-6-(2-fluoro-phenoxy)-1H-indazole | 340 |
| 3 | 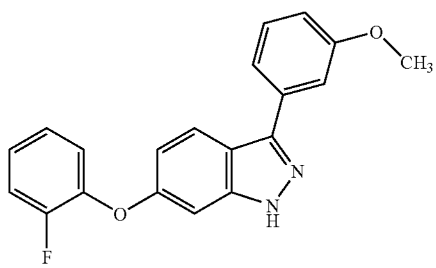 | 6-(2-Fluoro-phenoxy)-3-(3-methoxy-phenyl)-1H-indazole | 335 |
| 4 | 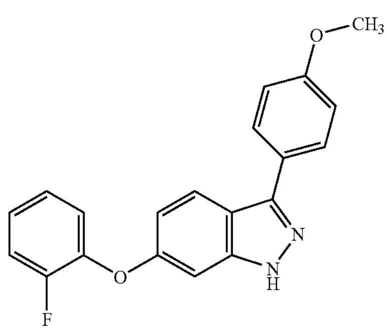 | 6-(2-Fluoro-phenoxy)-3-(4-methoxy-phenyl)-1H-indazole | 335 |
| 5 | 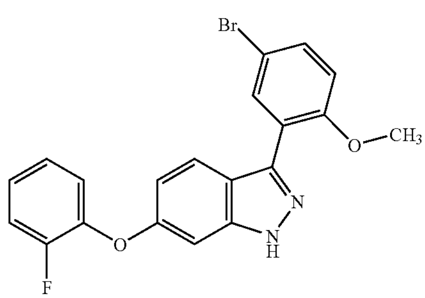 | 3-(5-Bromo-2-methoxy-phenyl)-6-(2-fluoro-phenoxy)-1H-indazole | 414 |
| 6 | 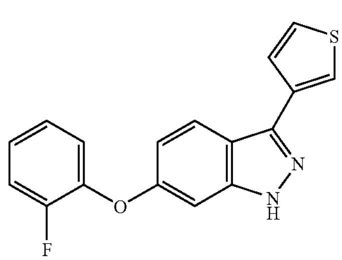 | 6-(2-Fluoro-phenoxy)-3-thiophen-3-yl-1H-indazole | 311 |

TABLE 1-continued
| # | Structure | Name (Autonom ™) | MP ° C. or M + H |
|---|---|---|---|
| 7 | 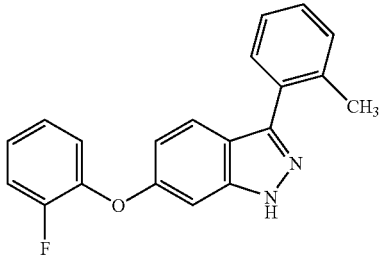 | 6-(2-Fluoro-phenoxy)-3-o-tolyl-1H-indazole | 319 |
| 8 | 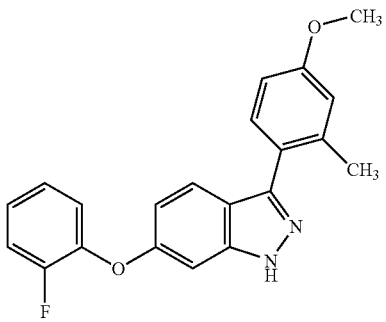 | 6-(2-Fluoro-phenoxy)-3-(4-methoxy-2-methyl-phenyl)-1H-indazole | 349 |
| 9 | 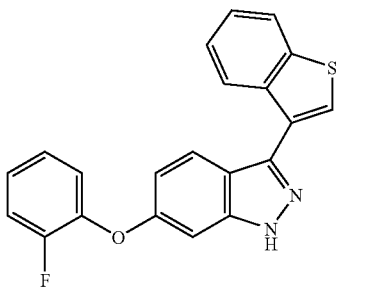 | 3-Benzo[b]thiophen-3-yl-6-(2-fluoro-phenoxy)-1H-indazole | 361 |
| 10 | 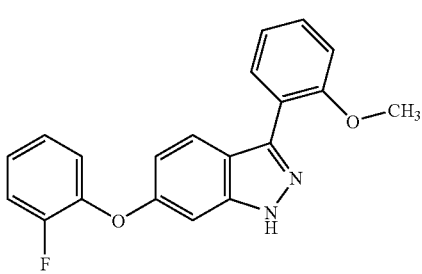 | 6-(2-Fluoro-phenoxy)-3-(2-methoxy-phenyl)-1H-indazole | 335 |
| 11 | 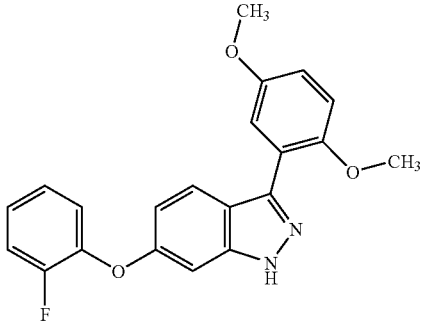 | 3-(2,5-Dimethoxy-phenyl)-6-(2-fluoro-phenoxy)-1H-indazole | 365 |

TABLE 1-continued

| # | Structure | Name (Autonom ™) | MP °C. or M + H |
|---|---|---|---|
| 12 | 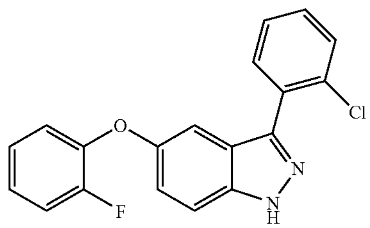 | 3-(2-Chloro-phenyl)-5-(2-fluoro-phenoxy)-1H-indazole | 340 |
| 13 | 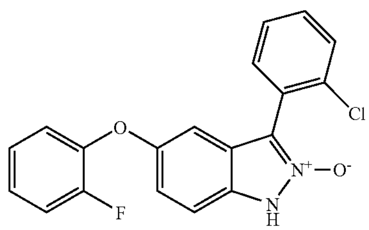 | 3-(2-Chloro-phenyl)-5-(2-fluoro-phenoxy)-1H-indazole 2-oxide | 356 |
| 14 | 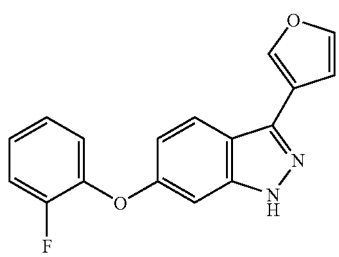 | 6-(2-Fluoro-phenoxy)-3-furan-3-yl-1H-indazole | 295 |
| 15 | 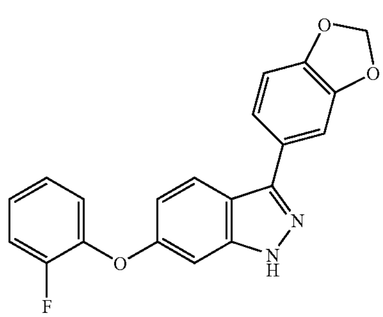 | 6-(2-Fluoro-phenoxy)-3-furan-3-yl-1H-indazole6-(2-Fluoro-phenoxy)-3-furan-3-yl-1H-indazole | 349 |
| 16 | 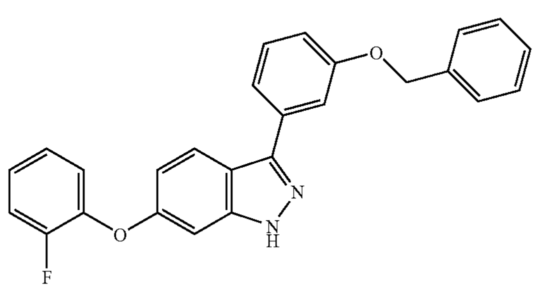 | 3-(3-Benzyloxy-phenyl)-6-(2-fluoro-phenoxy)-1H-indazole | 411 |

TABLE 1-continued

| # | Structure | Name (Autonom ™) | MP ° C. or M + H |
|---|---|---|---|
| 17 | 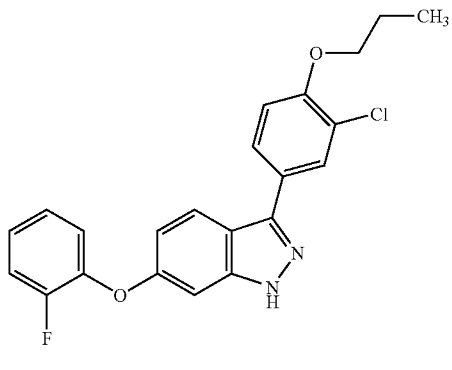 | 3-(3-Chloro-4-propoxy-phenyl)-6-(2-fluoro-phenoxy)-1H-indazole | 398 |
| 18 | 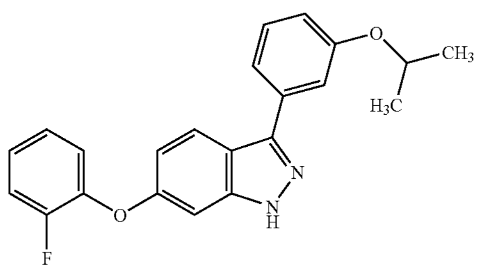 | 6-(2-Fluoro-phenoxy)-3-(3-isopropoxy-phenyl)-1H-indazole | 363 |
| 19 | 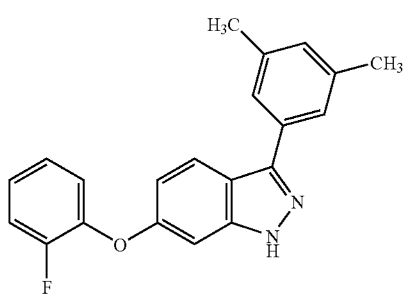 | 3-(3,5-Dimethyl-phenyl)-6-(2-fluoro-phenoxy)-1H-indazole | 333 |
| 20 | 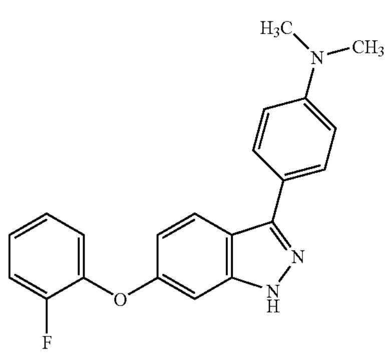 | {4-[6-(2-Fluoro-phenoxy)-1H-indazol-3-yl]-phenyl}-dimethyl-amine | 348 |

TABLE 1-continued
| # | Structure | Name (Autonom ™) | MP °C. or M + H |
|---|---|---|---|
| 21 | 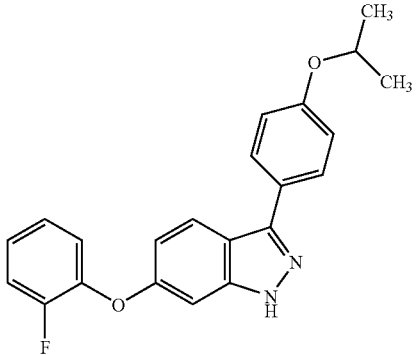 | 6-(2-Fluoro-phenoxy)-3-(4-isopropoxy-phenyl)-1H-indazole | 363 |
| 22 | 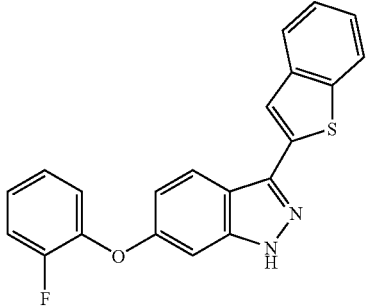 | 3-Benzo[b]thiophen-2-yl-6-(2-fluoro-phenoxy)-1H-indazole | 361 |
| 23 | 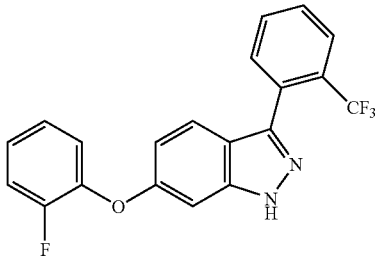 | 6-(2-Fluoro-phenoxy)-3-(2-trifluoromethyl-phenyl)-1H-indazole | 373 |
| 24 | 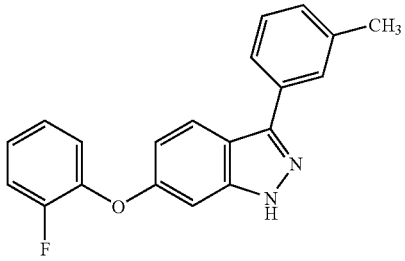 | 6-(2-Fluoro-phenoxy)-3-m-tolyl-1H-indazole | 319 |
| 25 | 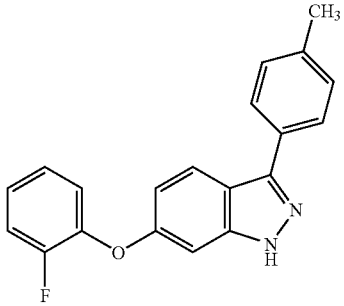 | 6-(2-Fluoro-phenoxy)-3-p-tolyl-1H-indazole | 319 |

TABLE 1-continued

| # | Structure | Name (Autonom ™) | MP ° C. or M + H |
|---|---|---|---|
| 26 | 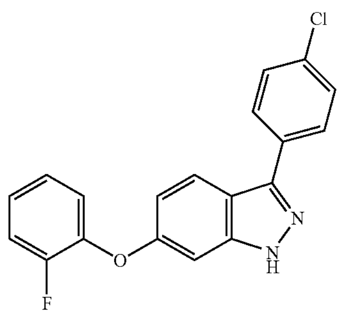 | 3-(4-Chloro-phenyl)-6-(2-fluoro-phenoxy)-1H-indazole | 181.0-181.7° C. |
| 27 | 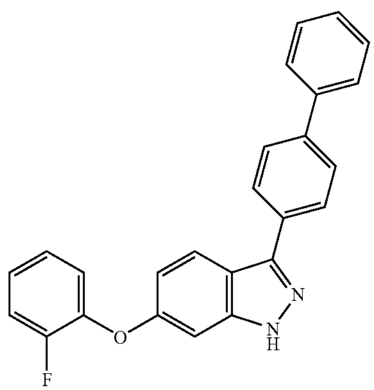 | 3-Biphenyl-4-yl-6-(2-fluoro-phenoxy)-1H-indazole | 381 |
| 28 | 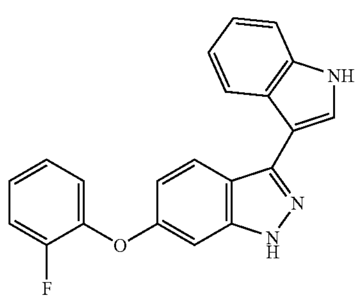 | 6-(2-Fluoro-phenoxy)-3-(1H-indol-3-yl)-1H-indazole | 344 |
| 29 | 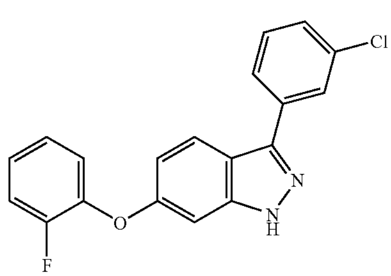 | 3-(3-Chloro-phenyl)-6-(2-fluoro-phenoxy)-1H-indazole | 340 |

TABLE 1-continued

| # | Structure | Name (Autonom ™) | MP ° C. or M + H |
|---|---|---|---|
| 30 | 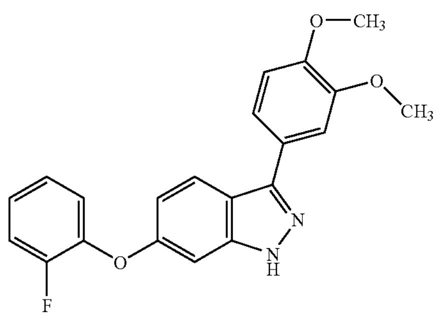 | 3-(3,4-Dimethoxy-phenyl)-6-(2-fluoro-phenoxy)-1H-indazole | 365 |
| 31 | 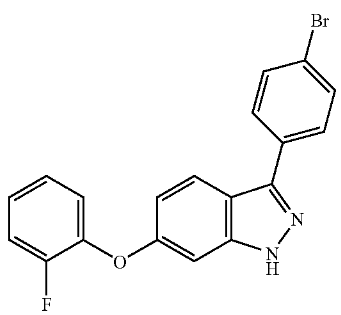 | 3-(4-Bromo-phenyl)-6-(2-fluoro-phenoxy)-1H-indazole | 384 |
| 32 | 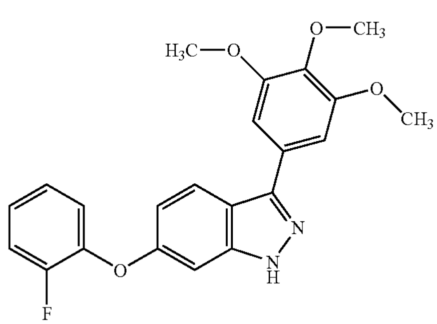 | 6-(2-Fluoro-phenoxy)-3-(3,4,5-trimethoxy-phenyl)-1H-indazole | 395 |
| 33 | 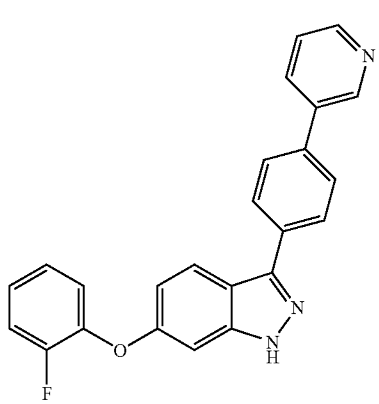 | 6-(2-Fluoro-phenoxy)-3-(4-pyridin-3-yl-phenyl)-1H-indazole | 195.0-198.2° C. |

TABLE 1-continued

| # | Structure | Name (Autonom ™) | MP ° C. or M + H |
|---|---|---|---|
| 34 | 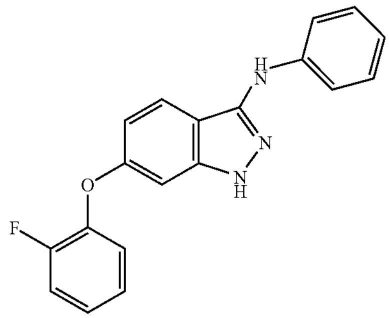 | [6-(2-Fluoro-phenoxy)-1H-indazol-3-yl]-phenyl-amine | 320 |
| 35 | 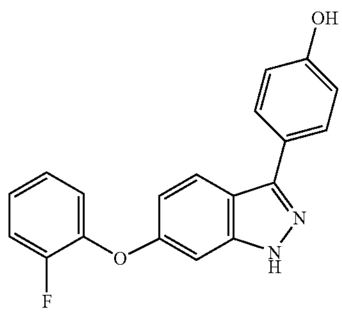 | 4-[6-(2-Fluoro-phenoxy)-1H-indazol-3-yl]-phenol | 321 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One of the specific methods for preparing pyrazolopyrimidine compounds of the invention is shown in Scheme I below, wherein PG is a protecting group.

Scheme I

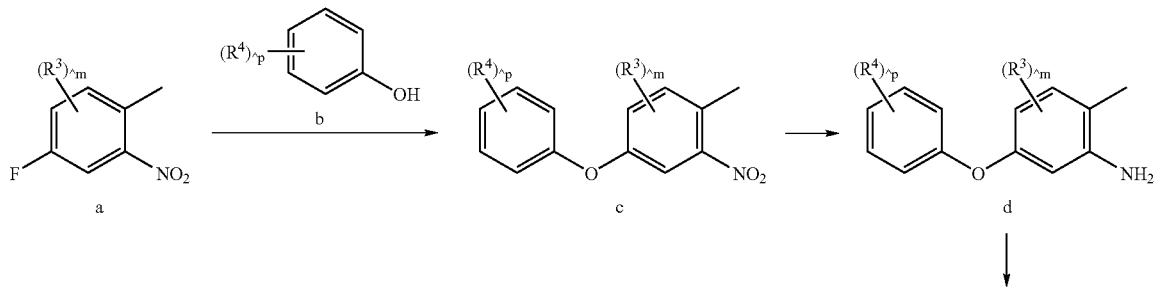

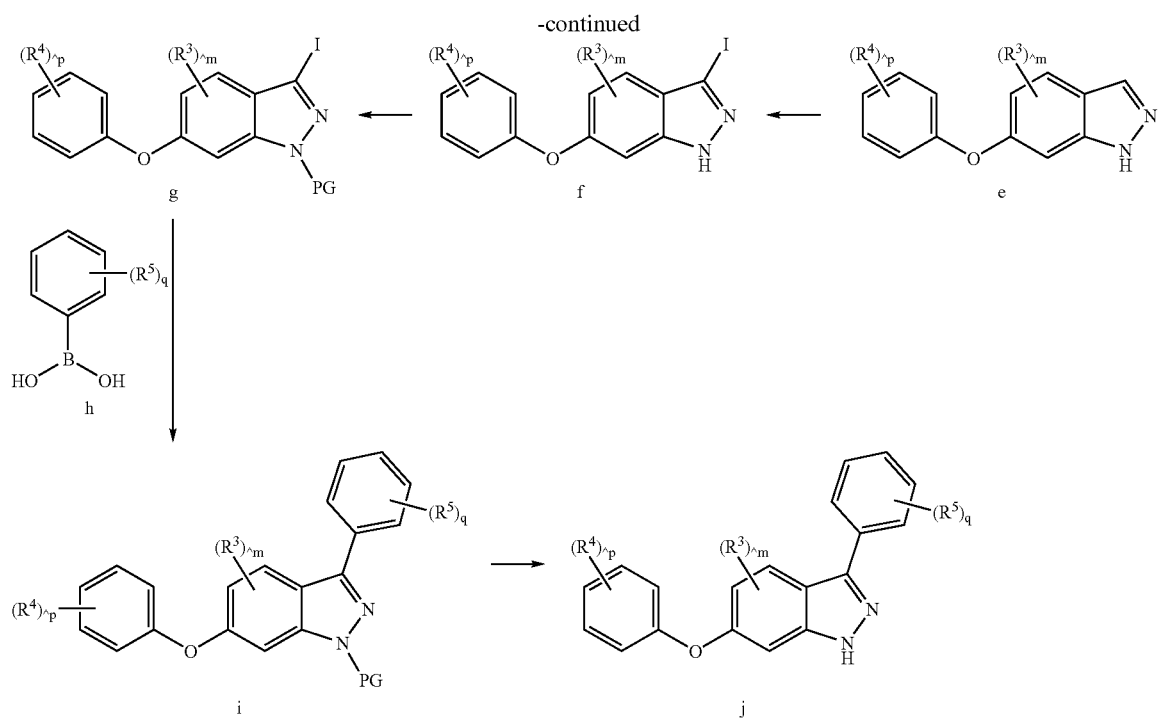

In Scheme I, fluoronitrotoluene a is reacted with phenol b in the presence of mild base such as potassium carbonate, to afford a phenoxy nitrotoluene c. Phenoxy nitrotoluene c is then reduced, using catalyzed hyrdogenation or othe reduction technique, to provide phenoxy aminotoluene d. Phenoxy aminotoluene d undergoes a cyclization reaction by treatment with isoamyl nitrate to form phenoxy indazole e. Phenoxy indazole e is subject to iodine under basic conditions to yield a phenoxy iodoindazine f, which is then protected via Boc, Fmoc or other suitable protection scheme, to afford a protected phenoxy iodoindazole g. The protected phenoxy iodoindazole g is treated with a phenyl boronic acid h in the presence of a suitable catalyst to form a phenoxy phenylindazole i, which is deprotected to provide an indazole derivative j in accordance with the invention.

One of skill in the art will understand that certain modifications to the above schemes are contemplated and within the scope of the present invention. For example, certain steps will involve the use of protecting groups for functional groups that are not compatible with particular reaction conditions. Various hydroxyaryl and hydroxyheteroaryl compounds may be used in place of phenol b, and various aryl and heteroaryl boronic acids may be used in place of phenyl boronic acid h.

More specific details for producing compounds of the invention are described in the Examples section below.

Pharmaceutical Compositions and Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone(1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.).

Example 1

This example illustrates a synthesis of 3-(2—Chloro-phenyl)-6-(2-fluoro-phenoxy)-1H-indazole following the procedure of Scheme I above.

Step 1. Preparation of
4-(2-Fluoro-phenoxy)-2-nitrotoluene

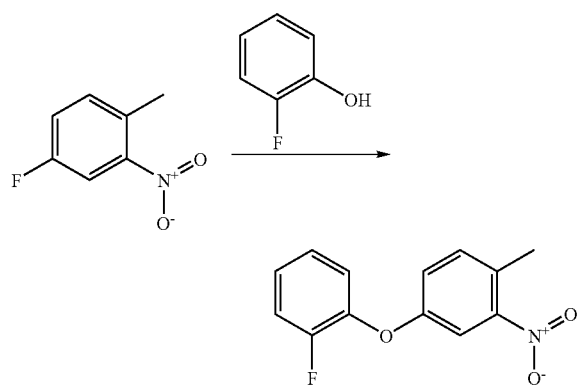

To 4-fluoro-2-nitrotoluene (25 g, 0.016 mol), 2-fluorophenol (15.8 mL, 0.017 mol) in NMP (350 mL) was added potassium carbonate (22.27 g, 0.016 mol) and the mixture was stirred at 160° C. for 48 h. After cooling at room temperature, water (350 mL) was added and the solution was extracted into ethyl acetate (2×150 mL). The combined organic extracts were dried over $Na_2SO_4$, filtered, concentrated and the residue was purified by flash chromatography eluting with Hex:EtOAc 95:5 to yield 15.17 g of 4-(2-fluoro-phenoxy)-2-nitrotoluene: MS: 248 (M+H).

Step 2. Preparation of
5-(2-Fluoro-phenoxy)-2-methyl-phenylamine

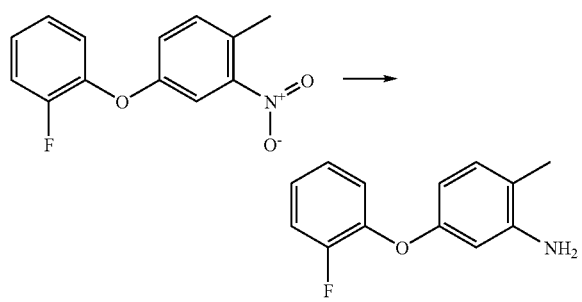

4-(2-fluoro-phenoxy)-2-nitrotoluene (15.17 g, 0,061 mol) and Pd/C (1.67 g) in ethanol (150 mL) were stirred under hydrogen atmosphere for 48 h, then the mixture was filtered through celite and the filtrate was concentrated under vacuum and purified by flash chromatography eluting with Hex: EtOAc 9:1 to afford 10.9 g of 5-(2-fluoro-phenoxy)-2-methyl-phenylamine: MS: 218 (M+H).

Step 3. Preparation of
6-(2-Fluoro-phenoxy)-1H-indazole

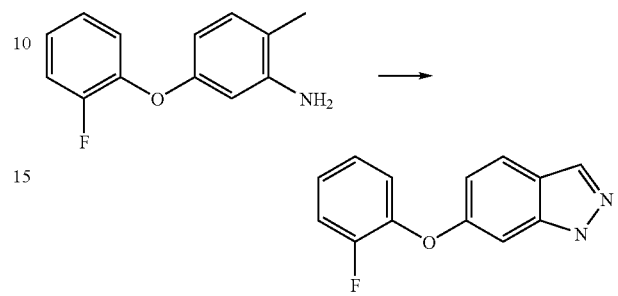

To a suspension of 5-(2-fluoro-phenoxy)-2-methyl-phenylamine (2.4 g, 11.04 mmol), acetic anhydride (3.36 g, 33.12 mmol) and potassium acetate anhydrous (1.10 g, 11.16 mmol) in benzene (36 mL) at 80° C. was added dropwise over 30 minutes isoamyl nitrite (2.22 mL, 16.56 mmol) and the reaction mixture was stirred at this temperature overnight. After cooling to room temperature, the precipitate formed was filtered and the filtrate was concentrated under vacuum and the residue treated with 5N HCl (4.5mL) then concentrated HCl (2.5 mL); the mixture was heated at 55° C. for 2.5 h then 60° C. for 15 min. The reaction was cooled to room temperature extracted into benzene (15 mL), the aqueous layer was basified with $NH_4OH$ the extracted into EtOAc (2×25 mL), the combined organic layers were dried over $Na_2SO_4$ filtered, concentrated and the residue was purified by flash chromatography eluting with Hex:EtOAc 7:3 to yield 1.8 g of 6-(2-fluoro-phenoxy)-1H-indazole: MS: 229 (M+H).

Step 4. Preparation of
6-(2-Fluoro-phenoxy)-3-iodo-1H-indazole

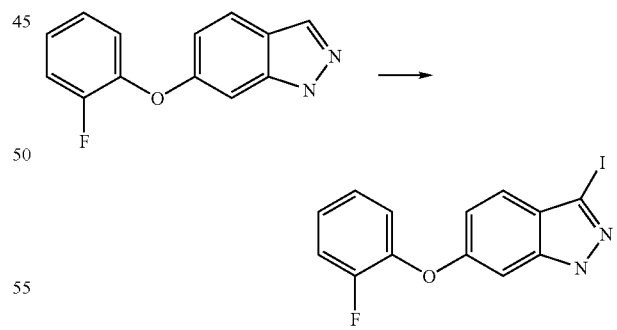

Iodine (1.53 g, 6.02 mmol) and potassium hydroxide pellets (805 mg, 14.3 mmol) were added successively into a DMF solution of 6-(2-Fluoro-phenoxy)-1H-indazole (1.35 g, 5.92 mmol) at room temperature under stirring. After 1.5 h the reaction was poured into sodium bisulfite solution and extracted into EtOAc (2×20 mL). The combined organic layers were dried over $Na_2SO_4$ filtered, concentrated and the residue was purified by flash chromatography eluting with Hex:EtOAc 9:1 to yield 1.9 g of 6-(2-fluoro-phenoxy)-3-iodo-1H-indazole: MS: 355 (M+H).

Step 5. Preparation of 6-(2-Fluoro-phenoxy)-3-iodo-indazole-1-carboxylic acid tert-butyl ester

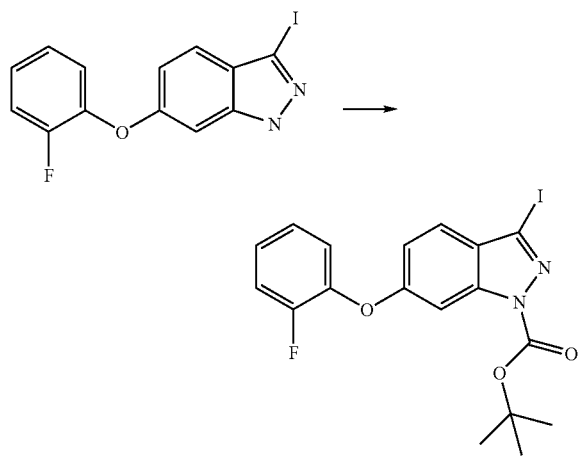

6-(2-Fluoro-phenoxy)-3-iodo-1H-indazole (1.9 g, 5.36 mmol), di-tert-butyl-dicarbonate (1.4 g, 6.43 mmol) and 4-dimethylaminopyridine (33 mg, 0.26 mmol) in THF (10 mL) was refluxed for 2.5 h. The reaction mixture was cooled to room temperature, concentrated under vacuum and the residue purified by flash chromatography Hex:EtOAc 9:1 to yield 2.4 g of 6-(2-fluoro-phenoxy)-3-iodo-indazole-1-carboxylic acid tert-butyl ester: MS: 455 (M+H).

Step 6. Preparation of 3-(2-Chloro-phenyl)-6-(2-fluoro-phenoxy)-indazole-1-carboxylic acid tert-butyl ester

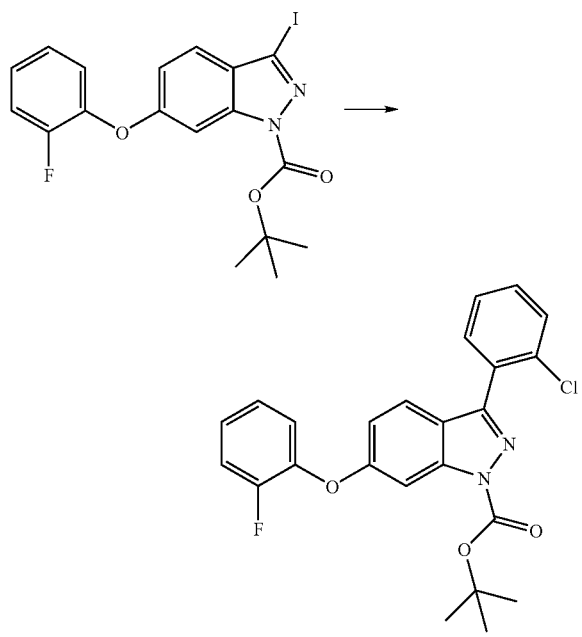

To a solution of (Ph$_3$P)$_4$Pd (36 mg, 0.03 mmol) in dioxane (4 mL) under Argon was added 6-(2-Fluoro-phenoxy)-3-iodo-indazole-1-carboxylic acid tert-butyl ester (140 mg, 0.3 mmol) and the solution was stirred for 10 min, then 2-chlorophenyl boronic acid (96.4 mg, 0.6 mmol) in ethanol (1.2 mL) was added. After 10 min potassium carbonate (132 mg, 0.9 mmol) in water (0.4 mL) was added and the mixture was stirred at 85° C. under Argon for 18 h. The mixture was cooled to room temperature, filtered through Celite, partitioned between water and EtOAc, the separated organic phase was dried over Na$_2$SO$_4$ filtered, concentrated and the residue was purified by flash chromatography eluting with Hex:EtOAc 9:1 to yield 90 mg of 3-(2-Chloro-phenyl)-6-(2-fluoro-phenoxy)-indazole-1-carboxylic acid tert-butyl ester: MS: 345 (M+H).

Step 7. Preparation of 3-(2-Chloro-phenyl)-6-(2-fluoro-phenoxy)-1H-indazole

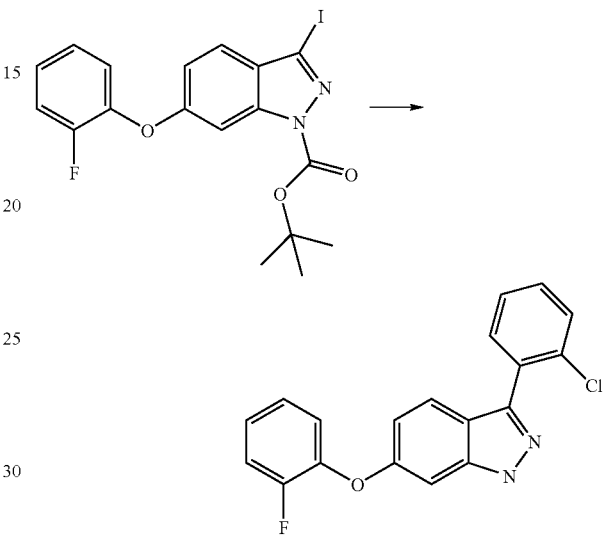

A solution of 3-(2-Chloro-phenyl)-6-(2-fluoro-phenoxy)-indazole-1-carboxylic acid tert-butyl ester (90 mg, 0.2 mmol) and sodium methoxide (22 mg, 0.41 mmol) in methanol (2 mL) was stirred at room temperature for 1 h, and then concentrated under vacuum. The residue was diluted with EtOAc, washed with water, dried over Na$_2$SO$_4$ filtered, concentrated and the residue was purified by flash chromatography eluting with Hex:EtOAc 4:1 to yield 42 mg of 3-(2-Chloro-phenyl)-6-(2-fluoro-phenoxy)-1H-indazole: MS (M+H)$^+$=339

Example 2

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Using the above procedure, the compounds of the invention were found to be inhibitors of p38 MAP kinase. For example, 4-[6-(2-Fluoro-phenoxy)-1H-indazol-3-yl]-phenol exhibited a p38 $IC_{50}$ (uM) of 0.028.

Example 3

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

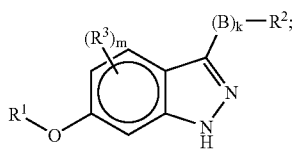

or pharmaceutically acceptable salts, solvates or prodrugs thereof,
wherein:
$R^1$ is aryl, aralkyl or cycloalkyl;
$R^2$ is aryl, or cycloalkyl;
m is from 0 to 4;
$R^3$ is hydrogen, alkyl, haloalkyl, cyano, nitro, amino, hydroxyl, alkoxy, hydroxycycloalkyl or —C(=O)—$R^a$,
wherein
$R^a$ is hydrogen, alkyl, heteroalkyl, aryl, or aralkyl; and
k is 0.

2. The compound of claim 1, wherein $R^1$ is optionally substituted phenyl.

3. The compound of claim 2, wherein $R^1$ is 2-halophenyl or 2,4-dihalophenyl.

4. The compound of claim 1, wherein $R^2$ is 2-chlorophenyl, 4-hydroxyphenyl, 4-methoxyphenyl, 4-benzyloxyphenyl, 3-benzyloxyphenyl, 4-dimethylaminophenyl, 4-aminophenyl, 4-fluorophenyl, 3-fluorophenyl, 2-fluorophenyl, 3-trifluoromethylphenyl, pyrid-3-yl, 4-(pyrid-2-yl)phenyl, 3-isopropoxyphenyl, 3,5-dimethylphenyl, 3-morpholinophenyl, 4-morpholinophenyl, 3-(4-methyl-piperazin-1-yl)-phenyl, 4-(4-methyl-piperazin-1-yl)-phenyl, N-methyl-N-(2-methoxyethyl)-phenyl, 2,4-difluorophenyl, 4-isopropyloxyphenyl, 3-(2-pyridin-2-yl-ethoxy)-phenyl, 3-chloro-4-propoxyphenyl, biphenyl, pyridin-3-ylphenyl, or 3,4,5-trimethoxyphenyl.

5. The compound of claim 1, wherein said compound is of the formula III:

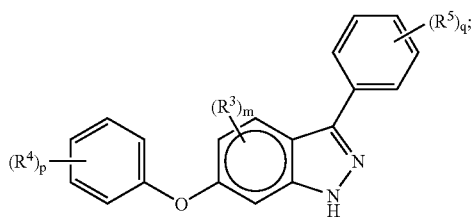

wherein:
p and q each independently is from 0 to 4;
each $R^4$ is independently halo, alkyl, alkoxy, haloalkyl, or cyano;
each $R^5$ is independently halo, alkyl, haloalkyl, cyano, heteroalkyl, heterocyclyl, hydroxycycloalkyl or —C(=O)—$R^c$,
wherein
$R^c$ is alkyl, heteroalkyl, aryl, aralkyl, heteroaryl or heterocyclyl; and
m and $R^3$ are as defined in claim 1.

6. The compound of claim 5, wherein said compound is of the formula IV:

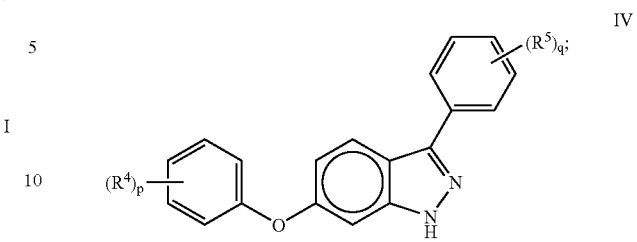

wherein p, q, $R^4$ and $R^5$ are as defined in claim 5.

7. The compound of claim 1, wherein said compound is selected from:
6-(2-Fluoro-phenoxy)-3-phenyl-1H-indazole;
3-(2-Chloro-phenyl)-6-(2-fluoro-phenoxy)-1H-indazole;
6-(2-Fluoro-phenoxy)-3-(3-methoxy-phenyl)-1H-indazole;
6-(2-Fluoro-phenoxy)-3-(4-methoxy-phenyl)-1H-indazole;
3-(5-Bromo-2-methoxy-phenyl)-6-(2-fluoro-phenoxy)-1H-indazole;
6-(2-Fluoro-phenoxy)-3-o-tolyl-1H-indazole;
6-(2-Fluoro-phenoxy)-3-(4-methoxy-2-methyl-phenyl)-1H-indazole;
6-(2-Fluoro-phenoxy)-3-(2-methoxy-phenyl)-1H-indazole;
3-(2,5-Dimethoxy-phenyl)-6-(2-fluoro-phenoxy)-1H-indazole;
3-(2-Chloro-phenyl)-5-(2-fluoro-phenoxy)-1H-indazole;
3-(3-Benzyloxy-phenyl)-6-(2-fluoro-phenoxy)-1H-indazole;
3-(3-Chloro-4-propoxy-phenyl)-6-(2-fluoro-phenoxy)-1H-indazole;
6-(2-Fluoro-phenoxy)-3-(3-isopropoxy-phenyl)-1H-indazole;
3-(3,5-Dimethyl-phenyl)-6-(2-fluoro-phenoxy)-1H-indazole;
{4-[6-(2-Fluoro-phenoxy)-1H-indazol-3-yl]-phenyl}-dimethyl-amine;
6-(2-Fluoro-phenoxy)-3-(4-isopropoxy-phenyl)-1H-indazole;
3-Benzo[b]thiophen-2-yl-6-(2-fluoro-phenoxy)-1H-indazole;
6-(2-Fluoro-phenoxy)-3-(2-trifluoromethyl-phenyl)-1H-indazole;
6-(2-Fluoro-phenoxy)-3-m-tolyl-1H-indazole;
6-(2-Fluoro-phenoxy)-3-p-tolyl-1H-indazole;
3-(4-Chloro-phenyl)-6-(2-fluoro-phenoxy)-1H-indazole;
3-Biphenyl-4-yl-6-(2-fluoro-phenoxy)-1H-indazole;
3-(3-Chloro-phenyl)-6-(2-fluoro-phenoxy)-1H-indazole;
3-(3,4-Dimethoxy-phenyl)-6-(2-fluoro-phenoxy)-1H-indazole;
3-(4-Bromo-phenyl)-6-(2-fluoro-phenoxy)-1H-indazole;
6-(2-Fluoro-phenoxy)-3-(3,4,5-trimethoxy-phenyl)-1H-indazole;
6-(2-Fluoro-phenoxy)-3-(4-pyridin-3-yl-phenyl)-1H-indazole; and
4-[6-(2-Fluoro-phenoxy)-1H-indazol-3-yl]-phenol.

8. A composition comprising:
(a) a pharmaceutically acceptable excipient; and
(b) a compound of claim 1.

* * * * *